US011827613B2

(12) United States Patent
Wang et al.

(10) Patent No.: US 11,827,613 B2
(45) Date of Patent: Nov. 28, 2023

(54) PROCESS AND SYSTEM TO MAKE OLEFIN EPOXIDES

(71) Applicant: ExxonMobil Technology Engineering Company, Annandale, NJ (US)

(72) Inventors: Kun Wang, Branchburg, NJ (US); Timothy D. Shaffer, Plainfield, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 24 days.

(21) Appl. No.: 17/597,887

(22) PCT Filed: Jul. 2, 2020

(86) PCT No.: PCT/US2020/040624
§ 371 (c)(1),
(2) Date: Jan. 28, 2022

(87) PCT Pub. No.: WO2021/021384
PCT Pub. Date: Feb. 4, 2021

(65) Prior Publication Data
US 2022/0169625 A1 Jun. 2, 2022

Related U.S. Application Data

(60) Provisional application No. 62/881,412, filed on Aug. 1, 2019.

(51) Int. Cl.
*C07D 305/12* (2006.01)

(52) U.S. Cl.
CPC .................. *C07D 305/12* (2013.01)

(58) Field of Classification Search
CPC .................................... C07D 305/12
See application file for complete search history.

(56) References Cited

U.S. PATENT DOCUMENTS

| | | |
|---|---|---|
| 2,356,459 A | 8/1944 | Kung |
| 2,450,116 A | 9/1948 | Caldwell |
| 2,450,131 A | 9/1948 | Hagemeyer, Jr. |
| 2,518,662 A | 8/1950 | Caldwell |
| 3,000,906 A | 9/1961 | Hasek et al. |
| 3,221,028 A | 11/1965 | Nations et al. |
| 3,291,810 A | 12/1966 | Edward |
| 3,326,938 A | 6/1967 | Lyle |
| 3,392,174 A | 7/1968 | Hildebrand |
| 3,524,866 A | 8/1970 | Klootwijk |
| 3,690,566 A | 9/1972 | Krauss et al. |
| 5,395,980 A | 3/1995 | Mueller et al. |
| 5,539,131 A | 7/1996 | Lin |
| 5,556,682 A | 9/1996 | Gavin et al. |
| 7,091,365 B2 | 8/2006 | Shan et al. |
| 8,445,703 B2 | 5/2013 | Allen et al. |
| 8,822,709 B2 | 9/2014 | Chewter et al. |
| 9,493,391 B2 | 11/2016 | Allen et al. |
| 9,637,423 B1 | 5/2017 | Wang et al. |
| 9,637,424 B1 | 5/2017 | Wang |
| 9,688,626 B2 | 6/2017 | Wang et al. |
| 10,023,533 B2 | 7/2018 | Wang |
| 2009/0076312 A1 | 3/2009 | Loescher et al. |
| 2013/0096329 A1 | 4/2013 | Chewter et al. |
| 2017/0023820 A1 | 1/2017 | Kwan et al. |
| 2018/0030015 A1 | 2/2018 | Farmer et al. |
| 2018/0297018 A1 | 10/2018 | Nyugen et al. |

FOREIGN PATENT DOCUMENTS

| | | |
|---|---|---|
| DE | 2201331 A1 | 7/1972 |
| GB | 1111945 A | 5/1968 |
| JP | 7306455 B2 | 1/1998 |
| JP | 7005540 B2 | 1/2022 |
| NL | 7100545 A | 7/1972 |
| WO | 2018203179 A1 | 11/2018 |

OTHER PUBLICATIONS

PCT/US2020/040624 International Search Report and Written Opinion dated Nov. 18, 2020.
Matsuyama, et al., "127 Effects of trialkyl borates on Mo(VI)-catalyzed epoxidation of less reactive unsaturated compounds using t-butyl hydroperoxide", Studies of Surface Science and Catalysis, 145.. 2003. 511-512.
Getzler, et al., "Synthesis of β-lactones: a highly active and selective catalyst for epoxide carbonylation", J. Am. Chem. Soc., 2002, 124(7), 1174-1175.
Mahadevan, et al., "[Lewis acid]+[Co(CO)4]—complexes: a versatile class of catalysts for carbonylative ring expansion of epoxides and aziridines", Angew. Chem. Int. Ed., 2002, 41, No. 15, 2781-2784.

*Primary Examiner* — Golam M Shameem
(74) *Attorney, Agent, or Firm* — SHOOK, HARDY & BACON L.L.P.

(57) ABSTRACT

A method may include: oxidizing iso-butane with oxygen to produce t-butyl hydroperoxide and t-butyl alcohol; dehydrating at least a portion of the t-butyl alcohol to produce di-tert-butyl ether and isobutylene; epoxidizing at least a portion of the isobutylene with the t-butyl hydroperoxide to produce isobutylene oxide and t-butyl alcohol; and carbonylating at least a portion of the isobutylene oxide with carbon monoxide to produce pivalolactone.

5 Claims, 1 Drawing Sheet

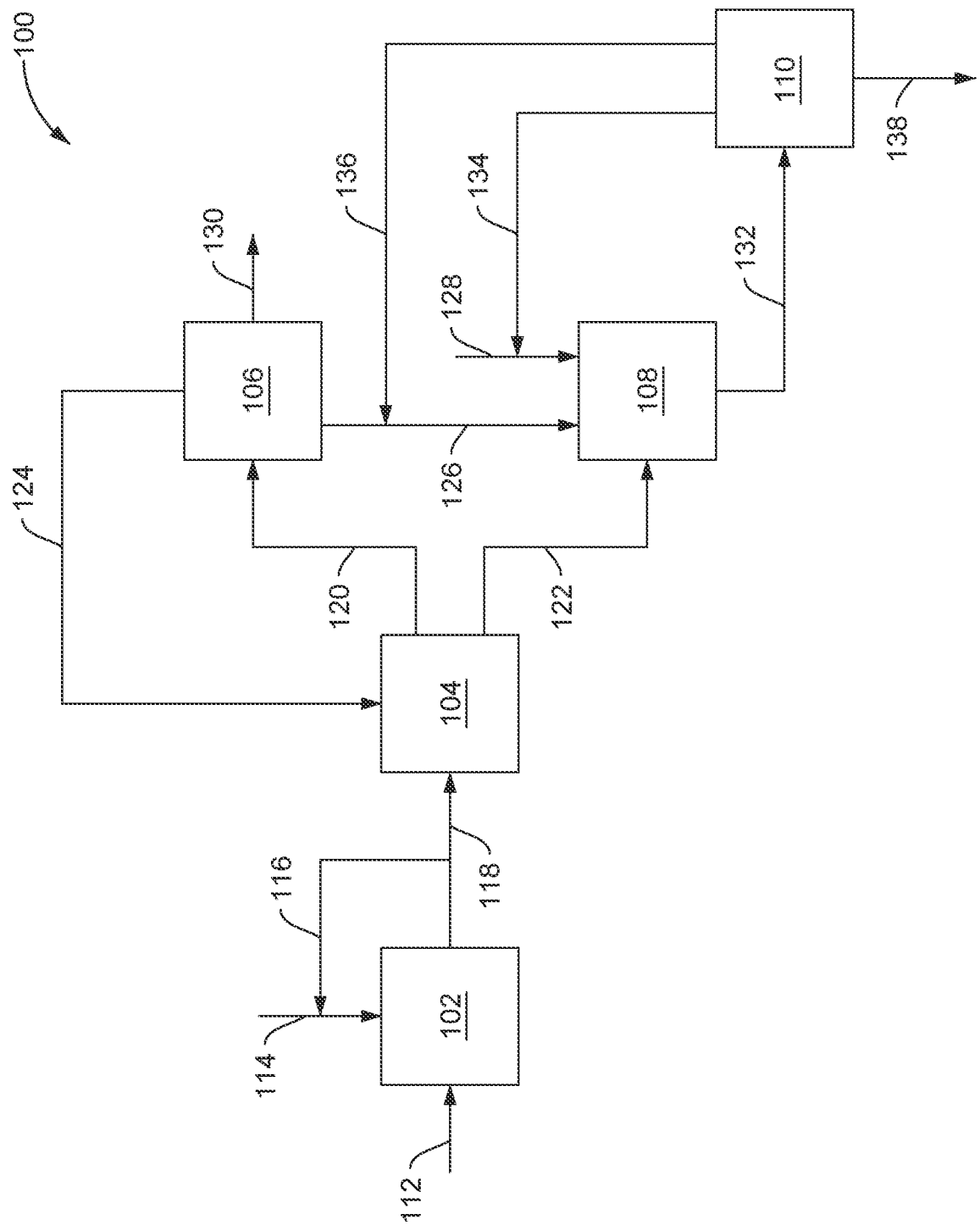

PROCESS AND SYSTEM TO MAKE OLEFIN EPOXIDES

CROSS-REFERENCE TO RELATED APPLICATIONS

This application is the 35 USC § 371 National Stage Application of PCT Application Number PCT/US2020/040624, filed on Jul. 2, 2020, which claims the benefit of U.S. Provisional Application No. 62/881,412, filed on Aug. 1, 2019, the entire contents of both of which are incorporated herein by reference.

FIELD

This application relates to processes and systems for producing substituted lactones from oxidative carbonylation of alkanes with three or more carbon atoms.

BACKGROUND

Lactone is a class of important chemical or chemical intermediate. For example, Pivalolactone (α,α-dimethyl-β-propiolactone) can be used as a monomer to synthesize linear polyesters including polypivalolactone (PPVL). PPVL may be prepared with a wide range of molecular weights from oligomers to polymers with molecular weights in the order of millions. PPVL has a high degree of crystallinity and may have desirable properties such as low glass transition temperature, chemical stability with resistance to water, acids, alkalis, solvents, bleaching agents, detergents, heat, and UV light. Some applications of PPVL may include fibers, molded articles, films, blends, and composites, for example. However, while PPVL may be a desirable polymer to synthesize, preparation of the monomer pivalolactone (PVL) typically involves the use of exotic materials such as ketenes, which may be extremely reactive and difficult to handle or may involve corrosive materials such as β-chlorocarboxylic acids.

Olefin epoxides are an important intermediate that can be converted to many useful products, for example, olefin epoxides may be converted to surfactants, detergents, esters, and epoxies. In some instances, isobutylene epoxide can be converted to lactone (by carbonylation) and further to polypivalolactone. Olefin epoxides can be produced by oxidation of olefins with an epoxidation agent. During the epoxidation, an oxygen atom is transferred from the epoxidation agent to C=C double bond in the olefins, thus forming a three-membered ring with two carbon and one oxygen. Suitable epoxidation agents may typically include peracids, hydroperoxides, hydrogen peroxide, and ozone, or $O_2$ (in the case of ethylene oxide). Existing technologies typically require olefins as feeds, which are produced by steam cracking, catalytic cracking, or catalytic dehydrogenation of alkanes. Since olefin generation from alkanes is a highly endothermic process, the processes to produce olefins are energy intensive with high carbon footprint. Therefore, it is desirable to use alkanes as the feed to produce olefin epoxides via oxidation using oxygen or air. Such an advantaged process to produce olefin epoxides leads to a desired process to prepare lactones via carbonylation of the olefin epoxides derived from oxidation of alkanes.

As discussed above, there may be two commercially available routes to synthesize the monomer pivalolactone (PVL) illustrated in Reactions 1 and 2. PVL may be considered a di-methyl substituted lactone.

Reaction 1

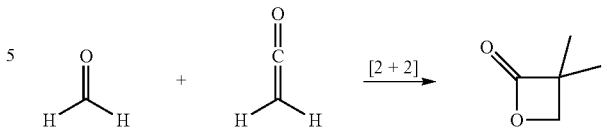

In Reaction 1, a carbonyl compound, such as formaldehyde, may be reacted with a ketene, such as dimethylketene to form the PVL monomer. Reaction 1 may be carried out the presence of an aprotic Lewis acid which may produce PVL by a 2+2 addition. The reaction conditions are typically about 50° C. in ethyl acetate or propyl acetate solvent in a weak Lewis acid such as zinc chloride ($ZnCl_2$). This reaction route typically requires the preparation and handling of the ketene as well as the use of formaldehyde. There may be some downsides to Reaction 1 such as difficulty in separating the product from reactants and water workup to quench the reactive dimethylketene and remove the Lewis acid followed by fractional distillation of the product. Reaction 1 may be expensive as catalyst loading may be high and the PVL purification may be difficult.

Reaction 2

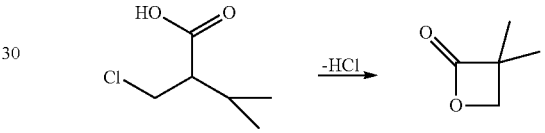

A reaction path to produce PVL on a larger scale than Reaction 1 is illustrated in Reaction 2. In Reaction 2, a β-chlorocarboxylic acid such as chloropivalic acid may undergo a ring closing reaction to form PVL. However, chloropivalic acid may be corrosive to metal surfaces, and chloropivalic acid may thermally polymerize to polypivalolactone (PPVL). There have been some efforts to suppress the tendency of chloropivalic acid to polymerize thermally or otherwise during synthesis by addition of additives such as boron trifluoride ($BF_3$) and tribenzylamine, phosphorus acids, phosphates, and potassium permanganate/sulfur dioxide mixtures. However, the thermodynamics and kinetics of the reaction dictate that the reaction temperature generally must be in excess of 160° C. which max exacerbate the aforementioned premature polymerization during synthesis. Furthermore, the ring closing reaction often produces caustic by-products which may be harmful to reactor equipment and may be difficult or expensive of which to dispose.

There may be other routes to produce PVL, such as the cyclization of hydroxyacids where the halogen of a β-chlorocarboxylic acid is instead replaced by a hydroxyl group. Such ring closing reactions may be conducted in a solvent with a base. Some exemplary solvents may include paraffin oils, phthalates, chloroform, water/methanol, and benzene/butanol, for example. Some exemplary bases may include sodium hydroxide, sodium hydrogen carbonate, lead oxide, and sodium methoxide, for example. For PVL synthesis, these methods are prone to produce a variety of side products including isobutyric acid, formaldehyde, and isobutylene, for example. Some efforts to mitigate the production of side products may include first converting 3-hydroxypivalic acid to 3-acetoxypivalic acid prior to ring close. While this modified synthesis may be effective in reducing the production of side products, it also complicates the synthesis by including an additional step to the procedure.

Another reaction path to PVL may include catalytic carbonylation of isobutylene oxide (IBO). For example, ionic complexes with [Co(CO)$_4$]$^-$ anion and aluminum salen cations which may catalyze carbonylation of IBO in solvents such as dimethoxy ethane [CH$_3$OCH$_2$CH$_2$OCH$_3$] or triglyme [CH$_3$OCH$_2$CH$_2$OCH$_2$CH$_2$OCH$_2$CH$_2$OCH$_3$], for example. Without being limited by theory, the solvent chosen may affect the yield and conversion of IBO to PVL. IBO may be produced from isobutylene, which may be produced from steam or catalytic cracking of crude oil, vacuum gas oil, or other hydrocarbon sources, or by the catalytic dehydrogenation of alkanes, all of which are energy intensive processes. Other substituted epoxides, such as cis-butene oxide, may be produced similarly.

Given the limitations and challenges of the forgoing processes, finding a means to produce lactones using a less energy-intensive processes is desirable.

SUMMARY

Disclosed herein is an example method including: introducing a branched alkane stream into an oxidation unit, the branched alkane stream including a branched alkane; oxidizing at least a portion of the branched alkane and generating at least an oxidized stream from the oxidation unit, the oxidized stream including an organic hydroperoxide and a branched alcohol; introducing at least a portion of the oxidized stream and a branched alkene stream into an epoxidation unit, the branched alkene stream including a branched alkene; epoxidizing at least a portion of the branched alkene with the organic hydroperoxide and generating a mixed intermediate product stream including a substituted olefin epoxide and additional branched alcohol; dehydrating at least a portion of the branched alcohol and generating at least a branched ether stream including a branched ether; introducing at least a portion of the mixed intermediate product stream, a carbon monoxide stream, and the branched ether stream into a carbonylation unit, the carbon monoxide stream including carbon monoxide and the branched ether stream including a branched ether; and carbonylating at least a portion of the substituted olefin epoxide with the carbon monoxide and generating a product stream including a substituted lactone.

Further disclosed herein is another example method including: oxidizing iso-butane with oxygen to produce t-butyl hydroperoxide and t-butyl alcohol; dehydrating at least a portion of the t-butyl alcohol to produce di-tert-butyl ether and isobutylene; epoxidizing at least a portion of the isobutylene with the t-butyl hydroperoxide to produce isobutylene oxide and t-butyl alcohol; and carbonylating at least a portion of the isobutylene oxide with carbon monoxide to produce pivalolactone.

Further disclosed herein is an example system including: an oxidation unit; an epoxidation unit, wherein an effluent stream from the oxidation unit is coupled to one or more inputs of the epoxidation unit; a dehydration unit, wherein an effluent stream from the epoxidation unit is coupled to one or more inputs of the dehydration unit; a carbonylation unit, wherein the effluent stream from the epoxidation unit is coupled to one or more inputs of the dehydration unit; and a separation unit, wherein an effluent stream from the carbonylation unit is coupled to one or more inputs of the separation unit.

BRIEF DESCRIPTION OF THE DRAWINGS

The drawing illustrates certain aspects of the present disclosure and should not be used to limit or define the disclosure.

The FIGURE is a schematic diagram of a process for production of substituted lactones in accordance with embodiments of the present disclosure.

DETAILED DESCRIPTION

This application relates to processes and systems for producing substituted lactones from oxidative carbonylation of alkanes with three or more carbon atoms.

There may be several potential advantages to the methods and systems disclosed herein, only some of which may be alluded to in the present disclosure. As discussed above, olefin epoxides can be an important intermediate in the production of many useful products which may include substituted lactones. Advantageously, embodiments provide processes and systems that react branched alkanes with oxygen for production of substituted olefin epoxides with three or more carbon atoms. Then the substituted olefin epoxide may be further reacted with carbon monoxide to produce a substituted lactone. The process and systems may be particularly advantageous as embodiments may produce substituted lactones in an integrated process that uses only branched alkanes, oxygen, and carbon monoxide to produce substituted lactones. Accordingly, the methods and systems disclosed may enable efficient large-scale production of substituted lactones from readily available materials, such as branched alkanes, oxygen, and carbon monoxide.

Embodiments may include an integrated process for production of substituted lactones by carbonylation of substituted olefin epoxides. The substituted olefin epoxide may be produced as an integrated part of the process alongside solvents required. The process may include the following steps: (1) oxidation of a branched alkane to produce an organic hydroperoxide and a branched alcohol; (2) epoxidizing a branched alkene with an organic hydroperoxide to produce a substituted olefin epoxide and a branched alcohol; (3) catalytically reacting a branched alcohol to form a branched alkene and branched ether; and (4) carbonylating a substituted olefin epoxide with carbon monoxide to produce a substituted lactone. The substituted olefin epoxide in step (2) may include three or more carbon atoms.

In Step (1), any suitable technique for oxidation of a branched alkane to produce an organic hydroperoxide and a branched alcohol may be used. By way of example, the oxidation may include reaction of a branched alkane and oxygen in the liquid phase. Reaction 3 shows a generalized oxidation of a branched alkane.

Reaction 3

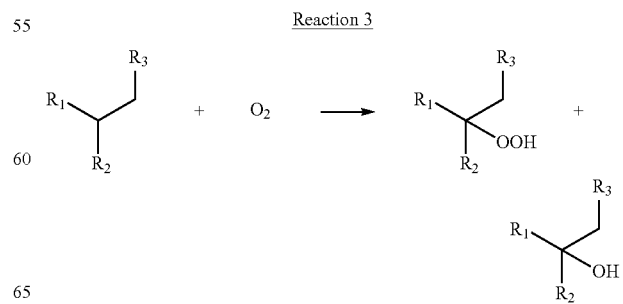

In Reaction 3, corresponding to Step (1) above, the branched alkane may include $R_1$, $R_2$, and $R_3$ substitution groups. $R_1$ and $R_2$ may be individually selected from H or a hydrocarbyl group containing 1 to 10 carbon atoms, wherein the hydrocarbyl group is linear, branched, or cyclic, and wherein the cyclic hydrocarbyl may be aromatic or non-aromatic. $R_3$ may be selected from H or a hydrocarbyl group containing 1 to 9 carbon atoms, wherein the hydrocarbyl group is linear, branched, or cyclic, and wherein the cyclic hydrocarbyl may be aromatic or non-aromatic. $R_1$, $R_2$, and $R_3$ may be individually selected such that not all three of $R_1$, $R_2$, and $R_3$ are H. In Reaction 3, the organic hydroperoxide and branched alcohol may include $R_1$, $R_2$, and $R_3$ groups that correspond to the $R_1$, $R_2$, and $R_3$ groups present in the branched alkane reactant. Any of a variety of branched alkanes may be used in the oxidation of Step (1). Suitable branched alkanes may have, for example, from 4 carbon atoms to 30 carbon atoms. Specific examples of suitable branched alkanes may include, but are not limited to, iso-butane, iso-pentane, iso-hexane, iso-heptane, and iso-octane, among others. Alternatively, $R_1$ and $R_2$ groups may be connected as part of a ring with 4 to 14 carbon atoms as shown in structure 1. The ring may be saturated or have multiple degrees of unsaturation without being aromatic.

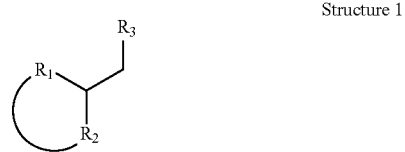

Structure 1

The oxidation of the branched alkane may be autocatalytic with no catalyst required. However, in some embodiments, a small amount of initiator may be used. For example, the initiator may be used in an amount of 50-10000 ppm. Suitable initiators may include, but are not limited to, the hydroperoxide generated from the branched alkane, t-butyl hydroperoxide, cumyl hydroperoxide, 1-phenylethyl hydroperoxide, di-t-butyl peroxide, di-cumyl peroxide, azobisisobutyronitrile (AIBN), 1,1'-azobis(cyanocyclohexane) (ACHN). In at least one embodiment, the reaction may be carried out in a reaction medium that is devoid of any substantial amount of metals in an ionic state, for example, to provide a reaction medium in which the organic hydroperoxide is stable. In at least one embodiment, water may be added to the reaction mixture in excess of that present as a result of the oxidation process. By way of example, water may be added in an amount of at least 1 wt % water based on the weight of the reaction mixture, for example, from about 1 wt % water to about 6 wt % water by weight of the reaction mixture. By way of further example, the oxidation may be carried out in a dense phase reaction mixture, that is the oxidation may be carried out above the critical pressure of the mixture and under a specified temperature (e.g., about 140° C. to about 170° C.) so that the reaction mixture behaves as a single, dense, quasi-liquid phase. In the dense-phase embodiments, for example, the oxidation may be conducted in a series of corresponding reaction zones. By way of yet another example, the oxidation exothermic heat of reaction may be removed by circulating a portion of the reaction mixture through an indirect heat exchange with the oxygen introduced by sparging into the cooled, circulating reaction mixture. In at least one embodiment, the oxidation of Step (1) may include the co-production of an alcohol. In some embodiments, the oxidation may be optimized to maximize the selectivity to the organic hydroperoxide.

Any suitable source of oxygen may be used in the oxidation of Step (1). In some examples it may be desired that the oxygen-to-hydrocarbon vapor ratio may be maintained outside the explosive regime. For example, source of oxygen may include air (approximately 21 vol % oxygen), a mixture of nitrogen and oxygen, or pure oxygen. The mixture of nitrogen and oxygen may contain, for example, about 2 vol % to about 20 vol % oxygen (or greater).

The oxidation of Step (1) may occur in an oxidation unit which includes equipment to facilitate the oxidation reaction. The oxidation unit may include a reactor and supporting equipment to control the oxidation reaction, add reactants, remove products, and maintain and control pressure and temperature. The oxidation step may occur at any suitable oxidation conditions, including temperature, pressure, and residence time. For example, the oxidation of step (1) may occur at a temperature of about 100° C. or greater. In some embodiments, the temperature of the oxidation may range from about 110° C. to about 200° C. or, alternatively, from about 130° C. to about 160° C. In some embodiments, the oxidation may be at a pressure of about 300 psig (2068 kpa) to about 800 psig (5526 kpa) or, alternatively, about 400 psig (2758 kpa) to about 600 psig (4199 kpa) or, alternatively, about 450 psig (3102 kpa) to about 550 psig (3792 kpa). In some embodiments, the residence time in the oxidation unit may be about 2 hours to about 24 hours, about 4 hours to about 10 hours, or about 6 hours to about 8 hours. The residence time may be selected to give a conversion to the organic hydroperoxide of about 15% to about 70%, about 20% to about 60%, or about 30% to about 50%. Where alcohol is co-product of the oxidation, the reaction conditions may be selected to provide a selectivity to the organic hydroperoxide of at least 50%, for example, of about 50% to about 80% with selectivity to the alcohol of about 20% to about 50%.

In Step (2), any suitable technique for epoxidation of the branched alkene with the organic hydroperoxide to produce a substituted olefin epoxide and a branched alcohol may be used. Reaction 4 shows a generalized epoxidation of the branched alkene.

Reaction 4

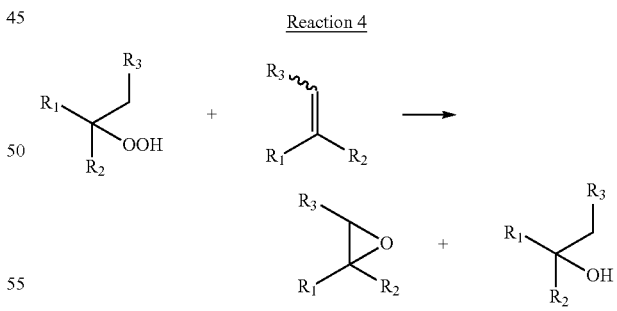

In Reaction 4, corresponding to Step (2) above, the organic hydroperoxide may be the organic hydroperoxide produced from Step (1). The branched alkene may be produced in Step (3) as will be explained in further detail below. The organic hydroperoxide and branched alkene may include $R_1$, $R_2$, and $R_3$ substitution groups which may correspond to the $R_1$, $R_2$, and $R_3$ groups from the branched alkane from Step (1).

In Step (2), the epoxidation may be carried out using a catalyst. In some embodiments, a soluble catalyst may be used that includes a metal, such as Re, Mo, Nb, Ti, Ta or mixtures thereof. An example of a suitable catalyst may have a Mo(VI)-oxo core such as molybdenum dioxide bis(acetylacetonate) or $MoO_2(acac)_2$ where acac is acetylacetonate. Any suitable amount of the catalyst may be used for catalyzing the epoxidation, including, an amount of about 0.001 mol % to about 5 mol % of the total moles of reactants, about 0.01 mol % to about 4 mol %, or about 0.1 mol % to about 2 mol %. Basic promoters may be also be used in the epoxidation. Examples of suitable basic promoters may include, but are not limited to, amines, phosphines, phosphine oxides, or alkyl borate esters. Any suitable amount of the basic promoter may be used, including about 0.001 mol % to about 10 mol % of the total moles of reactants, about 0.01 mol % to about 8 mol %, or about 0.1 mol % to about 5 mol %. The epoxidation may be performed with or without a solvent. Where used, suitable solvents may include, but are not limited to, methanol, ethanol, isopropyl alcohol, t-butyl alcohol. Other solvent such as ethers, hydrocarbons such as C10+ paraffins, cyclo-paraffins, aromatics such as toluene, xylenes, can also be used as long as it can provide the necessary solubility for the catalyst in the reaction mixture. Advantageously, the branched alcohol generated in Step (1) or as a co-product in Step (2) can be used as the solvent, avoiding the need for any additional chemicals in the process.

Any of a variety of branched alkene s may be used in the epoxidation of Step (2). Suitable branched alkene s may have, for example, from 4 carbon atoms to 30 carbon atoms. Specific examples of suitable branched alkene may include, but are not limited to, iso-butene, iso-pentene, iso-hexene, iso-heptene, and iso-octene, among others. In some embodiments, the branched alkene may include cyclic branches, which may be aromatic or non-aromatic. Examples of a suitable branched alkene s may include, for example, 4 carbon atoms, 5 carbon atoms, 6 carbon atoms, or 7 carbon atoms. In some embodiments, the branched alkene may be a combination of any of the previously mentioned branched alkenes. One example of a suitable branched alkene may include isobutylene. In some embodiments, the branched alkene may include cyclic branches, which may be aromatic or non-aromatic. In some examples, the branched alkene may be produced in-situ within the process in Step (3) as will be described in detail below.

The epoxidation of Step (2) may occur in an epoxidation unit which includes equipment to facilitate the epoxidation reaction. The epoxidation unit may include a reactor and supporting equipment to control the epoxidation reaction, add reactants, remove products, and maintain and control pressure and temperature. The epoxidation reaction may occur in a solution or a slurry at any suitable reaction conditions, including temperature, pressure, and residence time. For example, the epoxidation of step (2) may occur at a temperature of about 30° C. to about 200° C., about 130° C. to about 200° C., or about 75° C. to about 125° C. In some embodiments, the epoxidation may be at a pressure of about 15 psig (103 kpa) to about 1500 psig (10342 kpa), about 30 psig (207 kpa) to about 1000 psig (6895 kpa), or about 100 psig (689 kpa) to about 500 psig (3447 kpa). In some embodiments, the residence time in the epoxidation unit may be about 0.1 hours to about 24 hours, about 0.5 hours to about 12 hours, or about 1 hour to about 8 hours. The reaction conditions may be selected, for example, to give a conversion to the substituted olefin epoxide and a branched alcohol olefin epoxide of about 90% or greater and selectivity to the olefin epoxide of about 50% or greater.

In Step (3), the branched alcohol produced in Step (1) and/or Step (2) may be catalytically reacted to form a branched alkene and branched ether. Reaction 5 shows a generalized catalytic reaction of the branched alcohol.

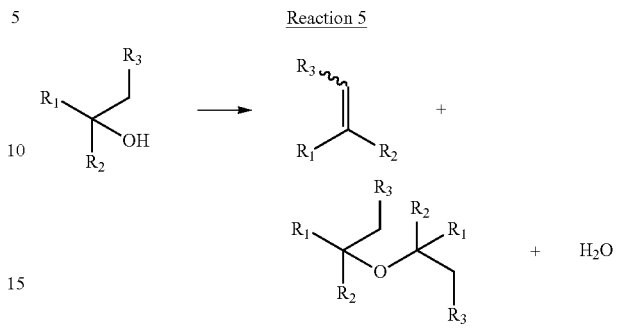

Reaction 5

In Reaction 5, corresponding to Step (3) above, the branched alcohol may be the branched alcohol produced in Step (1) and/or Step (2). The branched alcohol may include $R_1$, $R_2$, and $R_3$ substitution groups which may correspond to the $R_1$, $R_2$, and $R_3$ groups from the branched alkane from Step (1).

Reaction 5 may be considered a dehydration reaction of the branched alcohol which produces the branched alkene, branched ether, and water as products. The branched alkene may be the branched alkene utilized in Step (2) above and the branched ether may be the solvent utilized in Step (2) or Step (4) in the carbonylation reaction. The dehydration may be performed in a dehydration unit which includes equipment to facilitate the dehydration reaction. The dehydration unit may include a reactor and supporting equipment to control the dehydration reaction, add reactants, remove products, and maintain and control pressure and temperature. The dehydration reaction may occur in a solution or a slurry at any suitable reaction conditions, including temperature, pressure, and residence time.

The branched ether of Reaction 5 may be an intermediate reaction product in the dehydration reaction and the ratio of branched alkane to branched ether in the product may be adjusted depending on reaction conditions, for example. The molar ratio of branched ether to branched alkene may be in the range of about 0.01 to about 100. Alternatively, the molar ratio of the branched ether to branched alkene may be in the range of about 0.02 to about 50, about 0.05 to about 20, about 0.1 to about 10, or about 0.2 to about 5.

The dehydration may be carried out, for example, in any suitable reactor with any suitable catalyst. An acid catalyst may be used, for example, to catalyze the dehydration. Suitable acid catalyst may include, but are not limited to, crosslinked polystyrene resins containing sulfonic acid groups, carboxylic acid groups, or both sulfonic acid groups and carboxylic acid groups, or sulfonated fluoropolymers. Other acid catalysts may include acids such sulfuric acid, sulfonic acid, or phosphoric acid (neat or solid-supported on silica, alumina, or clay), alumina, aluminosilicates, acidic clay, zeolites (natural or synthetic), silicoaluminophosphates (SAPO), acidic ionic liquids, or acids, such as aluminum chloride or boron trifluoride.

The dehydration of Step (3) may be performed, for example, in the vapor phase at any suitable reaction conditions, including temperature, pressure, and residence time. For example, the dehydration of Step (3) may occur at a temperature of about 150° C. to about 450° C. or, alternatively, about 200° C. to about 350° C. In some embodiments, the dehydration be at a pressure of about 100 psig (103 kpa) to about 500 psig (10342 kpa), about 100 psig (207 kpa) to about 400 psig (6895 kpa), or about 150 psig (689 kpa) to about 300 psig (3447 kpa). In some embodiments, the residence time in the dehydration reactor may be about 1 second to 5 hours or, alternatively, about 5 seconds to 2 hours, or about 10 seconds to 1 hour. The reaction conditions may be selected, for example, to give a conversion to the hydrocarbon of about 80% or greater, or 85% higher, or 90% or higher.

In Step (4), the substituted olefin epoxide produced in Step (2) may be catalytically reacted with carbon monoxide to form a substituted lactone. Reaction 6 shows a generalized catalytic reaction of an olefin epoxide with carbon monoxide.

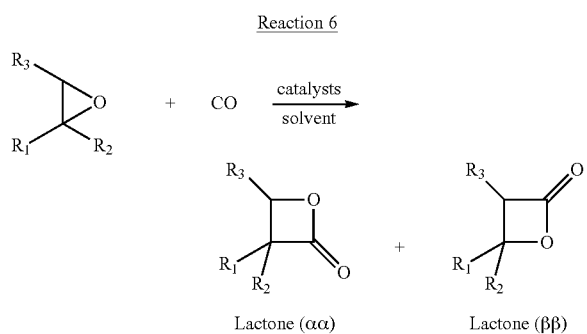

In Reaction 6, corresponding to Step (4) above, the substituted olefin epoxide may be the substituted olefin epoxide produced in Step (2). The substituted olefin epoxide may include $R_1$, $R_2$, and $R_3$ substitution groups which may correspond to the $R_1$, $R_2$, and $R_3$ groups from the branched alkane from Step (1). The lactones produced may be of the α-α form or β-β form, wherein the ratios produced may be controlled through catalyst selection and tuning of reaction conditions.

The reaction of the substituted olefin epoxide with carbon monoxide may occur in a carbonylation unit includes equipment to facilitate the carbonylation reaction. The epoxidation unit may include a reactor and supporting equipment to control the carbonylation reaction, add reactants, remove products, and maintain and control pressure and temperature. The substituted olefin epoxide from Step (2) may be combined with carbon monoxide and introduced into the carbonylation unit. Further, the branched ether from Step (3) may be introduced into the carbonylation unit as a solvent. The reactor in the carbonylation unit may include a catalyst capable of facilitating the carbonylation reaction at the operating temperature and pressure of the reactor.

In some embodiments, a suitable catalyst may include a cation portion linked to a solid support via an organic linker. The solid support may include any inert oxide such as silica, alumina, titania, zirconia, magnesia, non-acidic clay, aluminophosphate, or reticular support such as metal organic frameworks and zinc imidazolic frameworks for example. The catalyst may further include an anion portion which is electrostatically connected with the cation portion. The cationic portion may include a metal center and may further include an organic ligand bound to the metal center that sterically excludes molecules other than the oxygen of the substituted olefin epoxide from interacting with the metal. Steric exclusion of molecules other than oxygen may allow the anion portion of the catalyst to attack the tertiary carbon of the substituted olefin epoxide thereby allowing carbon monoxide insertion. Ring closure and ejection of the substituted lactone produced may regenerate the catalyst. The inclusion of a solid catalyst in the reactor may allow heterogeneous catalysis to take place which may allow for ready separation of products as compared to processes which utilize homogeneous catalysts. The solid catalyst may have minimal leaching into the reaction mixture due to the strong interaction between the bonded metal and the support and similarly strong electrostatic interaction between the metal and the anion.

The carbonylation reaction may occur in a solution or a slurry at any suitable reaction conditions, including temperature, pressure, and residence time. For example, the carbonylation of Step (4) may occur at a temperature of about 50° C. to about 100° C., about 60° C. to about 95° C., or about 70° C. to about 90° C. In some embodiments, the epoxidation may be at a pressure of about 500 psig (3447 kpa) to about 2000 psig (13790 kpa), about 750 psig (5171 kpa) to about 1500 psig (10342 kpa), or about 1000 psig (6895 kpa) to about 1500 psig (10342 kpa). In some embodiments, the residence time in the carbonylation unit may be about 0.1 hours to about 50 hours, about 0.5 hours to about 40 hours, or about 1 hour to about 36 hours. The reaction conditions and catalyst may be selected, for example, to give a conversion of the substituted olefin epoxide about 90%, 95%, 99%, or greater and selectivity to the substituted lactone of about 90%, 95%, 99%, or greater.

The net reaction of Steps (1)-(4) are illustrated in Reaction 7 below.

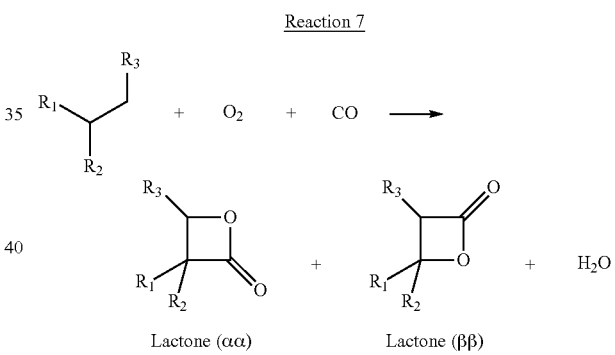

In Reaction 7, corresponding to Steps (1)-(4) described above, substituted lactones may be produced by an integrated process whereby common refinery streams such as branched alkanes, oxygen, and carbon monoxide may be reacted. The integrated process may recycle unreacted branched alkanes and unreacted carbon monoxide. Furthermore, the integrated process may allow production of a branched ether which may be utilized as a solvent within the integrated process. Generation of the solvent in-situ allows for a closed loop solvent solution whereby any solvent required is generated without the need for addition of an external solvent. Depending on the chemical identity of the solvent, there may also be commercial value in producing the solvent alongside the substituted lactone.

An embodiment may include production of pivalolactone from isobutane, oxygen, and carbon monoxide. In the present embodiment, the branched alkane is isobutane which may be considered to have $R_1$ and $R_2$ methyl substitutions and $R_3$ hydrogen substitution. A first step in the present embodiment may include oxidation of isobutane as illustrated in Reaction 8, corresponding to Step (1) described above.

Reaction 8

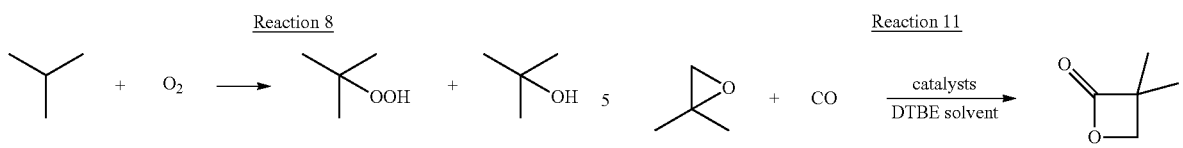

In Reaction 8, the oxidation of isobutane may proceed according the methods described above. The oxidation reaction may produce t-butyl hydroperoxide and t-butyl alcohol as products. A second step in the present embodiment may include the epoxidation of isobutene with t-butyl hydroperoxide as illustrated in Reaction 9, corresponding to Step (2) described above.

Reaction 9

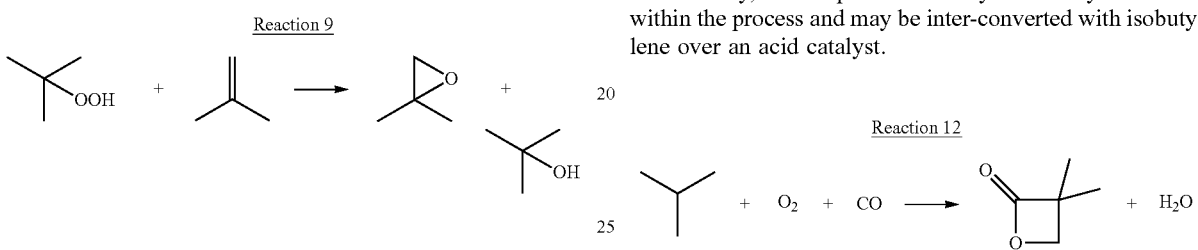

In Reaction 9, the epoxidation may proceed according to the methods described above. The epoxidation reaction may produce isobutylene oxide with t-butyl alcohol as a co-product. A third step in the present embodiment may include catalytic dehydration of t-butyl alcohol illustrated in Reaction 10, corresponding to Step (3) described above.

Reaction 10

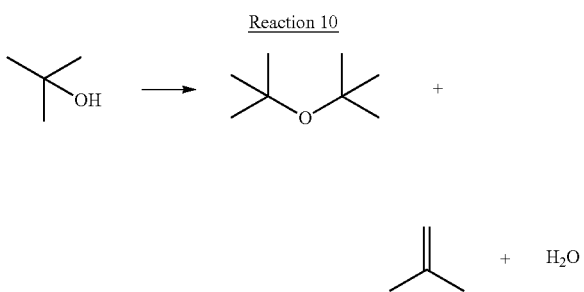

In Reaction 10, the catalytic dehydration may proceed according to the methods described above. The catalytic dehydration reaction may produce di-tert-butyl ether, isobutylene, and water as products. Di-tert-butyl-ether produced in Reaction 10 may advantageously be used as the solvent in downstream processes. There may be several advantages to utilizing di-tert-butyl ether including, but not limited to, that the solvent necessary for the carbonylation reaction may be generated from the available materials thereby eliminating the need for a foreign solvent, the boiling point of di-tert-butyl ether (107° C.) is high enough to allow elevated temperature for the step of carbonylation, produced pivalolactone and di-tert-butyl ether may be readily separated by distillation, and the dehydration conditions may be readily adjusted to meet the demand of makeup di-tert-butyl ether (DTBE) needed. The isobutylene produced in Reaction 10 may be used in Reaction 9. A fourth step in the present embodiment may include carbonylation of the isobutylene oxide as illustrated in Reaction 11, corresponding to Step (3) described above.

Reaction 11

In Reaction 11, the carbonylation reaction may proceed according to the methods described above. The carbonylation reaction may produce pivalolactone as a product. The DTBE solvent may be removed from the reaction mixture leaving pivalolactone as the product. Thus, the net reaction is converting isobutane, oxygen, and carbon monoxide to pivalolactone and water as shown in Reaction 12. Additionally, DTBE production may be readily controlled within the process and may be inter-converted with isobutylene over an acid catalyst.

Reaction 12

The FIGURE illustrates an embodiment of a process 100 for producing substituted lactones. As illustrated, process 100 may include oxidation unit 102, epoxidation unit 104, dehydration unit 106, carbonylation unit 108, and separation unit 110. Process 100 may begin with introduction of oxygen stream 112 and branched alkane stream 114 into oxidation unit 102. Oxygen stream 112 may be any source of oxygen described above including, air, pure oxygen, or oxygen enriched air, for example. Branched alkane stream 114 may include any of the previously described branched alkanes. Oxidation unit 102 may include a reactor where the reactions of Step (1) may be performed. Stream 118 may exit oxidation unit as a product stream. Stream 118 may include unreacted branched alkane, oxygen and other gasses introduced alongside the oxygen, and products organic hydroperoxide and branched alcohol. Stream 118 may be stripped of unreacted branched alkane, oxygen, and other gasses in a stripping unit (not shown) such that a majority of stream 118 introduced into epoxidation unit 104 is organic hydroperoxide and branched alcohol. Stripping unit may include any units capable of removing at least a portion of unreacted reactants such as, without limitation, flash drums and stripping columns for example.

Branched alkene stream 124 and stream 118 may be introduced into epoxidation unit 104. Branched alkene stream 124 may include a branched alkene generated in dehydration unit 106. Epoxidation unit 104 may include a reactor whereby the reactions of Step (2), described above, may be performed. The branched alcohol from stream 118 may be utilized as a solvent within epoxidation unit 104 to solubilize and bring into contact the branched alkene and organic hydroperoxide. As described above, the branched alkene and organic hydroperoxide may be reacted to form a substituted olefin epoxide and branched alcohol. An effluent from the reactor of epoxidation unit 104 may include the branched alcohol, organic hydroperoxide, branched alkene, and substituted olefin epoxide. The substituted olefin epoxide may be separated from the branched alcohol and unreacted branched alkene and organic hydroperoxide in a distillation column, for example, to generate substituted olefin epoxide stream 122 containing a majority of the substituted olefin epoxide generated in epoxidation unit 104 and branched alcohol stream 120 containing a majority of the branched alcohol from the effluent of the reactor of epoxidation unit 104.

Branched alcohol stream 120 may be introduced into dehydration unit 106. Dehydration unit 106 may include a reactor whereby the reactions of Step (3), described above, may be performed. In dehydration unit 106 the branched alcohol may be catalytically reacted to form the branched alkene, a branched ether, and water. The products of the dehydration reaction may be separated by distillation, for example, to form water stream 130, branched alkene stream 124, and branched ether stream 126. Branched alkene stream 124 may be conveyed to an introduced to epoxidation unit 104 and branched ether stream may be introduced to carbonylation unit 108.

Substituted olefin epoxide stream 122, branched ether stream 126, and carbon monoxide stream 128 may be introduced into carbonylation unit 108. Carbonylation unit 108 may include a reactor whereby the reactions of Step (4), described above, may be performed. In carbonylation unit 108 branched ether provided by branched ether stream 126 may act as a solvent to bring into contact the substituted olefin epoxide from substituted olefin epoxide stream 122 and carbon monoxide from carbon monoxide stream 128. The olefin epoxide and carbon monoxide may be reacted to produce a substituted lactone. Effluent stream 132 from the reactor of carbonylation unit 108 may include a mixture of unreacted carbon monoxide, substituted lactone, and branched ether. Effluent stream 132 may be conveyed to an introduced into separation unit 110 which may include equipment for separating the substituted lactone product. The unreacted carbon monoxide may be separated from a bulk liquid phase including the substituted lactone and branched ether in a flash drum, for example, to produce recycle carbon monoxide stream 134 which may be recycled back to carbonylation unit 108. The remaining liquid phase including substituted lactone and branched ether may be separated by distillation, for example, to produce substituted lactone stream 138 and recycle branched ether stream 136 which may be recycled back to carbonylation unit 108.

Accordingly, the preceding description describes examples of processes and systems for producing substituted lactones from oxidative carbonylation of alkanes with three or more carbon atoms. The processes and systems disclosed herein may include any of the various features disclosed herein, including one or more of the following embodiments.

Embodiment 1. A method including: introducing a branched alkane stream into an oxidation unit, the branched alkane stream including a branched alkane; oxidizing at least a portion of the branched alkane and generating at least an oxidized stream from the oxidation unit, the oxidized stream including an organic hydroperoxide and a branched alcohol; introducing at least a portion of the oxidized stream and a branched alkene stream into an epoxidation unit, the branched alkene stream including a branched alkene; epoxidizing at least a portion of the branched alkene with the organic hydroperoxide and generating a mixed intermediate product stream including a substituted olefin epoxide and additional branched alcohol; dehydrating at least a portion of the branched alcohol and generating at least a branched ether stream including a branched ether; introducing at least a portion of the mixed intermediate product stream, a carbon monoxide stream, and the branched ether stream into a carbonylation unit, the carbon monoxide stream including carbon monoxide and the branched ether stream including a branched ether; and carbonylating at least a portion of the substituted olefin epoxide with the carbon monoxide and generating a product stream including a substituted lactone.

Embodiment 2. The method of embodiment 1 wherein the branched alkane has the form of:

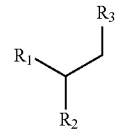

wherein, $R_1$ and $R_2$ are individually selected from H or a first hydrocarbyl group containing 1 to 10 carbon atoms, wherein the first hydrocarbyl group is linear, branched, cyclic and non-aromatic, or cyclic and aromatic, and wherein $R_3$ selected from H or a second hydrocarbyl group containing 1 to 9 carbon atoms, wherein the second hydrocarbyl group is linear, branched, cyclic and non-aromatic, or cyclic and aromatic, and wherein $R_1$, $R_2$, and $R_3$ are not each H.

Embodiment 3. The method of embodiment 1 wherein the branched alkane has the form of:

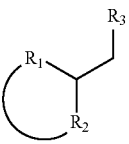

wherein $R_1$ and $R_2$ groups are connected by a ring of 4 to 14 carbon atoms, and wherein $R_3$ is selected from H or a hydrocarbyl group containing 1 to 9 carbon atoms, and wherein the hydrocarbyl group is linear, branched, cyclic and non-aromatic, or cyclic and aromatic.

Embodiment 4. The method of any of embodiments 1-3 further including introducing an oxygen stream including oxygen into the oxidation unit, wherein the step of oxidation comprises autocatalytic oxidation.

Embodiment 5. The method of any of embodiments 1~4 wherein the oxidized stream further comprises unreacted branched alkane, and wherein the method further comprises: removing at least a portion of the unreacted branched alkane from the oxidized stream before the step of introducing at least a portion of the oxidized stream into the epoxidation unit; and recycling the portion of the unreacted branched alkane to the oxidation unit.

Embodiment 6. The method of any of embodiments 1-5 wherein the step of epoxidizing is performed in a solution with a homogeneous catalyst and wherein the branched alcohol is the only solvent present in the solution.

Embodiment 7. The method of any of embodiments 1-6 wherein the step of dehydrating at least a portion of the branched alcohol comprises: introducing at least a portion of the mixed intermediate product stream into a dehydration unit and dehydrating at least a portion of the branched alcohol to generate the branched alkene stream and the branched ether stream.

Embodiment 8. The method of embodiment 7 wherein the dehydrating is catalyzed by an acid catalyst, and wherein the dehydrating occurs in a vapor phase.

Embodiment 9. The method of any of embodiments 1-8 wherein the step of epoxidation is performed in a reactor including a catalyst, and wherein the branched ether is the only solvent present in the reactor.

Embodiment 10. The method of any of embodiments 1-9 further including: separating at least a portion of the substituted lactone from the product stream.

Embodiment 11. The method of embodiment 10 wherein the product stream further comprises carbon monoxide and branched ether, and wherein the method further comprises separating at least a portion of the carbon monoxide and the branched ether from the product stream and recycling the separated carbon monoxide and the separated branched ether to the carbonylation unit.

Embodiment 12. A method including: oxidizing iso-butane with oxygen to produce t-butyl hydroperoxide and t-butyl alcohol; dehydrating at least a portion of the t-butyl alcohol to produce di-tert-butyl ether and isobutylene; epoxidizing at least a portion of the isobutylene with the t-butyl hydroperoxide to produce isobutylene oxide and t-butyl alcohol; and carbonylating at least a portion of the isobutylene oxide with carbon monoxide to produce pivalolactone.

Embodiment 13. The method of embodiment 12 wherein the step of oxidizing iso-butane comprises: introducing iso-butane and oxygen into an oxidation unit; and autocatalytically oxidizing the iso-butane with oxygen at a temperature of about 110° C. to about 150° C. and a pressure of about 2068 kPa to about 5515 kPa.

Embodiment 14. The method of any of embodiments 12-13 wherein the step of dehydrating t-butyl alcohol comprises: introducing at least a portion of the t-butyl alcohol produced from the step of oxidizing, at least a portion of the t-butyl alcohol produced from the step of epoxidizing, or both, into a dehydration unit; and catalytically dehydrating at least a portion of the t-butyl alcohol with an acid catalyst at a temperature of about 150° C. to about 450° C. and a pressure of about 700 kPa to about 3450 kPa.

Embodiment 15. The method of any of embodiments 12-14 wherein the step of epoxidizing isobutylene comprises: introducing at least a portion of the isobutylene produced from the step of oxidation and at least a portion of the t-butyl hydroperoxide produced from the step of dehydrating into an epoxidation unit; and catalytically epoxidizing at least a portion of the isobutylene with at least a portion of the t-butyl hydroperoxide at a temperature of about 30° C. to about 200° C. and a pressure of about 103 kPa to about 10342 kPa.

Embodiment 16. The method of any of embodiments 12-15 wherein the step of carbonylating isobutylene oxide comprises: introducing at least a portion of the isobutylene oxide produced from the step of epoxidizing, at least a portion of the di-tert-butyl ether produced from the step of dehydrating, and the carbon monoxide into a carbonylation unit; and catalytically carbonylating at least a portion of the isobutylene oxide with at least a portion of the carbon monoxide.

Embodiment 17. A system including: an oxidation unit; an epoxidation unit, wherein an effluent stream from the oxidation unit is coupled to one or more inputs of the epoxidation unit; a dehydration unit, wherein an effluent stream from the epoxidation unit is coupled to one or more inputs of the dehydration unit; a carbonylation unit, wherein the effluent stream from the epoxidation unit is coupled to one or more inputs of the carbonylation unit; and a separation unit, wherein an effluent stream from the carbonylation unit is coupled to one or more inputs of the separation unit.

18. The system of embodiment 17 wherein: further including a recycle separation unit, wherein the effluent stream from the oxidation unit is coupled to one or more inputs of the recycle separation unit and an effluent stream from the recycle separation unit is coupled to one or more inputs of the oxidation unit.

19. The system of any of embodiments 17-18 wherein an effluent stream from the dehydration unit is coupled to at least one of one or more inputs of the epoxidation unit or one or more inputs of the carbonylation unit.

20. The system of any of embodiments 17-19 wherein an effluent stream from the separation unit is coupled to one or more inputs of the carbonylation unit.

While the disclosure has been described with respect to a number of embodiments and examples, those skilled in the art, having benefit of this disclosure, will appreciate that other embodiments can be devised which do not depart from the scope and spirit of the disclosure as disclosed herein. Although individual embodiments are discussed, the present disclosure covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the disclosure, additionally, they do not exclude impurities and variances normally associated with the elements and materials used.

All numerical values within the detailed description and the claims herein modified by "about" or "approximately" with respect the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

The invention claimed is:

1. A method comprising:
   oxidizing iso-butane with oxygen to produce t-butyl hydroperoxide and t-butyl alcohol;
   dehydrating at least a portion of the t-butyl alcohol to produce di-tert-butyl ether and isobutylene;
   epoxidizing at least a portion of the isobutylene with the t-butyl hydroperoxide to produce isobutylene oxide and t-butyl alcohol; and
   carbonylating at least a portion of the isobutylene oxide with carbon monoxide to produce pivalolactone.

2. The method of claim 1 wherein the step of oxidizing iso-butane comprises:
   introducing iso-butane and oxygen into an oxidation unit; and
   autocatalytically oxidizing the iso-butane with oxygen at a temperature of about 110° C. to about 150° C. and a pressure of about 2068 kPa to about 5515 kPa.

3. The method of claim 1 wherein the step of dehydrating t-butyl alcohol comprises:
   introducing at least a portion of the t-butyl alcohol produced from the step of oxidizing, at least a portion of the t-butyl alcohol produced from the step of epoxidizing, or both, into a dehydration unit; and catalytically dehydrating at least a portion of the t-butyl alcohol with an acid catalyst at a temperature of about 150° C. to about 450° C. and a pressure of about 700 kPa to about 3450 kPa.

4. The method of claim 1 wherein the step of epoxidizing isobutylene comprises:

introducing at least a portion of the isobutylene produced from the step of oxidation and at least a portion of the t-butyl hydroperoxide produced from the step of dehydrating into an epoxidation unit; and catalytically epoxidizing at least a portion of the isobutylene with at least a portion of the t-butyl hydroperoxide at a temperature of about 30° C. to about 200° C. and a pressure of about 103 kPa to about 10342 kPa.

5. The method of claim 1 wherein the step of carbonylating isobutylene oxide comprises:

introducing at least a portion of the isobutylene oxide produced from the step of epoxidizing, at least a portion of the di-tert-butyl ether produced from the step of dehydrating, and the carbon monoxide into a carbonylation unit; and catalytically carbonylating at least a portion of the isobutylene oxide with at least a portion of the carbon monoxide.

* * * * *